US009243222B2

United States Patent
El-Etr et al.

(10) Patent No.: US 9,243,222 B2
(45) Date of Patent: Jan. 26, 2016

(54) COMPOSITIONS AND METHODS FOR PATHOGEN TRANSPORT (71) Applicant: Lawrence Livermore National Security, LLC, Livermore, CA (US)

(72) Inventors: Sahar El-Etr, Milpitas, CA (US); George R. Farquar, Livermore, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 88 days.

(21) Appl. No.: 14/148,484

(22) Filed: Jan. 6, 2014

(65) Prior Publication Data

US 2015/0191690 A1    Jul. 9, 2015

(51) Int. Cl.
*A61B 10/00* (2006.01)
*C12Q 1/70* (2006.01)
(Continued)

(52) U.S. Cl.
CPC .............. *C12N 1/20* (2013.01); *C12M 23/34* (2013.01); *C12M 33/02* (2013.01); *C12N 1/04* (2013.01); *C12N 1/10* (2013.01)

(58) Field of Classification Search
CPC ................................ A61B 10/00; C12Q 1/70
USPC ......................................................... 422/413
See application file for complete search history.

(56) References Cited

U.S. PATENT DOCUMENTS

| | | | | |
|---|---|---|---|---|
| 2,034,986 A | * | 3/1936 | Mislowitzer | B01L 7/04 126/263.01 |
| 3,450,129 A | * | 6/1969 | Brewer | A61B 10/02 600/572 |

(Continued)

FOREIGN PATENT DOCUMENTS

| | | | | |
|---|---|---|---|---|
| CN | 201158655 Y | * | 11/2007 | ............... C12M 1/26 |
| DE | 202007001898 U1 | * | 4/2007 | ............... C12M 1/24 |

(Continued)

OTHER PUBLICATIONS

Carvalho, F. et al, Current Microbiology, 2008, vol. 57, pp. 297-300, Occurance and Diversity of Legionellaceae in Polar Lakes of the Antarctic Peninsula.*

(Continued)

*Primary Examiner* — Albert Navarro
*Assistant Examiner* — Ginny Portner
(74) *Attorney, Agent, or Firm* — Foley & Lardner LLP (57) ABSTRACT

This disclosure provides a method for transporting a pathogen under ambient conditions, by culturing the pathogen with an amoeba under conditions that favor the incorporation of the pathogen into a trophozoite, starving the amoeba until it encysts, then culturing under conditions that favor conversion of the amoeba back to a trophozoite. In one aspect, the conditions that favor incorporation of the pathogen into the cyst of the amoeba comprises contacting the pathogen with the amoeba in an iron rich environment. Virus and/or bacteria are pathogens that can be transported by the disclosed method. Amoeba that are useful in the disclosed methods include, without limitation *Acanthamoeba castellanii, Hartmannella vermiformis* and *Naegleria gruberi*. The disclosed methods have utility in: transporting pathogens from military field hospitals and clinics to the laboratory; transporting pathogens from global satellite laboratories to clinical laboratories; long term storage of pathogens; enriching contaminated patient samples for pathogens of interest; biosurveillance and detection efforts.

12 Claims, 3 Drawing Sheets

Modified Cryogenic Vial
107
Rich Medium (108)
Membrane (103)
Amoeba Cysts in buffer (102)
Luer-lock (105)
Swab (106)
104
103
102
101

(51) Int. Cl.
*C12N 1/20* (2006.01)
*C12N 1/04* (2006.01)
*C12N 1/10* (2006.01)
*C12M 1/00* (2006.01)
*C12M 1/30* (2006.01)

(56) References Cited

U.S. PATENT DOCUMENTS

| | | | | |
|---|---|---|---|---|
| 3,890,204 A * | 6/1975 | Avery | A61B 10/0096 | 206/229 |
| 3,918,435 A * | 11/1975 | Beall | A61B 10/0096 | 600/572 |
| 4,014,746 A * | 3/1977 | Greenspan | A61B 10/0096 | 435/243 |
| 4,184,483 A * | 1/1980 | Greenspan | A61B 10/0096 | 435/304.2 |
| 4,448,534 A * | 5/1984 | Wertz | C12M 41/36 | 356/435 |
| 4,770,853 A * | 9/1988 | Bernstein | G01N 33/5302 | 422/413 |
| 4,813,432 A * | 3/1989 | Saint-Amand | A61B 10/0096 | 206/363 |
| 5,494,829 A * | 2/1996 | Sandstrom | G01N 21/21 | 356/364 |
| 5,891,709 A * | 4/1999 | Stern | C12N 1/04 | 435/252.1 |
| 6,617,146 B1 * | 9/2003 | Naccarato | C12M 33/04 | 435/243 |
| 8,068,991 B2 * | 11/2011 | Jung | G01N 33/5302 | 424/184.1 |
| 8,551,471 B2 * | 10/2013 | Filutowicz | A01N 63/00 | 424/93.1 |
| 8,979,784 B2 * | 3/2015 | Triva | | 600/569 |
| 2002/0084277 A1 * | 7/2002 | Mullens | F17C 3/08 | 220/560.04 |
| 2003/0157728 A1 * | 8/2003 | Uhl | A61B 10/0051 | 436/177 |
| 2004/0009519 A1 * | 1/2004 | Snaidr | C12Q 1/6893 | 435/6.11 |
| 2004/0214316 A1 * | 10/2004 | O'Connell | A61B 10/0096 | 435/309.1 |
| 2004/0254250 A1 * | 12/2004 | Whitekettle | A01N 47/44 | 514/635 |
| 2004/0267181 A1 * | 12/2004 | Tuite | A61B 10/02 | 604/1 |
| 2005/0273921 A1 * | 12/2005 | Mattson, Jr. | A61H 33/6063 | 4/541.1 |
| 2006/0246423 A1 * | 11/2006 | Adelson | C12Q 1/04 | 435/5 |
| 2007/0148724 A1 * | 6/2007 | Salter | B01L 3/5029 | 435/32 |
| 2007/0292195 A1 * | 12/2007 | May | A45D 34/04 | 401/134 |
| 2007/0292941 A1 * | 12/2007 | Handique | B01L 3/5027 | 435/288.7 |
| 2008/0031903 A1 * | 2/2008 | Gambotto | A61K 9/0048 | 424/400 |
| 2008/0183396 A1 * | 7/2008 | Jung | G01N 33/5302 | 702/19 |
| 2009/0298051 A1 * | 12/2009 | Salter | C12Q 1/10 | 435/5 |
| 2010/0112725 A1 * | 5/2010 | Babu | G01N 33/558 | 436/518 |
| 2010/0119417 A1 * | 5/2010 | Motadel | B01L 3/00 | 422/400 |
| 2011/0190146 A1 * | 8/2011 | Boehm | B01L 3/502784 | 506/7 |
| 2011/0239791 A1 * | 10/2011 | Fici | A01N 1/0268 | 73/863.11 |
| 2011/0250222 A1 * | 10/2011 | Greub | G01N 33/56927 | 424/190.1 |
| 2013/0031646 A1 * | 1/2013 | Ledbetter | A61K 49/0008 | 800/9 |
| 2014/0252237 A1 * | 9/2014 | Weinstein | C12Q 1/04 | 250/341.8 |
| 2014/0308661 A1 * | 10/2014 | Holmes | G01N 35/00 | 435/6.1 |
| 2014/0328800 A1 * | 11/2014 | Plasson | C12R 1/90 | 424/93.1 |
| 2015/0191690 A1 * | 7/2015 | El-Etr | C12N 1/20 | 435/235.1 |
| 2015/0218613 A1 * | 8/2015 | De Forest | C12Q 1/04 | 435/5 |

FOREIGN PATENT DOCUMENTS

| | | | | |
|---|---|---|---|---|
| GB | 2333609 | * | 7/1999 | G02C 13/00 |
| WO | 94/16743 | * | 8/1994 | A61L 2/18 |
| WO | 2005/049856 | * | 6/2005 | C12Q 1/04 |
| WO | 2007/131138 | * | 11/2007 | A61B 17/50 |

OTHER PUBLICATIONS

Hryniewiecka, L et al, Biochemical and Biophysical Research Communications, vol. 93(1), Mar. 13, 1980, pp. 141-148, Necessity of Iron for the alternative Respiratory Pathway in Acanthamoeba Castellanii.*
Abd, Hadi et al, Applied and Environmental Microbiology, vol. 69(1), Jan. 2003, pp. 600-606, Survival and Growth of Francisella tularensis in Acanthamoeba castellanii.*
Taylor, Mark et al, Endosymbiotic bacteria associated with nematodes, ticks and amoebae, FEMS Immunology and Medical Microbiology, vol. 64, pp. 21-31, 2012.*
Pushkareva, Valentina I et al, BMC Microbiology, 2010, vol. 10(26), pp. 1-11, Listeria monocytogenes virulence factor Listeriolysin O favors bacterial growth in co-culture with the ciliate Tetrahymena pyriformis, causes protozoan encystment and promotes bacterial survival inside cysts.*
Kumar, Raman et al, Recent Advances in the Treatment of Acanthamoegba Keratitis, Clinical Infectious Diseases, 2002, vol. 35, pp. 434-441.*
Khunkitti, W et al, Journal of Infection, 1998, vol. 36, pp. 43-48, Acanthamoeba castellanii: Growth, Encystment, Excystment and Biocide Susceptibility.*
Greub, Gilbert et al, Clinical Microbiology Reviews, Apr. 2004, vol. 17(2), pp. 413-433, Microorganisms Resistant to Free-Living Living Amoebae.*
Greub, Gilbert et al, Amoebae-resisting Bacteria Isolated from Human Nasal Swabs by Amoebal Coculture, Emerging Infectious Diseases, vol. 10(3), Mar. 2004, pp. 470-477.*
Agrell, I.P. S. 1971, vol. 118, pp. 142-146, Z. Zellforsch. The growth promoting action of Iron upon Acanthamoeba.*
Neff, R.J et al, Chapter 4, Induction of Synchronous Encystment (Differentiation) in *Acanthamoeba* sp. from Methods in Cell Physiology, pp. 55-83, (Prescott DN, ed.), Academic, New York, 1964.*
Cirillo et al., "Growth of Legionella pneumophila in Acanthamoeba castellanii enhances invasion". Infect Immun 62(8): 3254-3261 (1994).
El-Etr et al., "Francisella tularensis type A strains cause the rapid encystment of Acanthamoeba castellanii and survive in amoebal cysts for three weeks postinfection". Appl Environ Microbiol 75(23):7488-7500 (2009).
Goy et al., "The Neff strain of Acanthamoeba castellanii, a tool for testing the virulence of *Mycobacterium kansasii*". Res Microbiol 158: 393-397 (2007).
Greub et al., "Microorganisms resistant to free-living amoebae." Clin Microbiol Rev 17: 413-433 (2004).
Rodriguez-Zaragoza, "Ecology of free-living amoebae". Crit Rev Microbiol 20: 225-241 (1994).

* cited by examiner

COMPOSITIONS AND METHODS FOR PATHOGEN TRANSPORT

STATEMENT OF FEDERAL SUPPORT

The United States Government has rights in the invention pursuant to Contract No. DE-AC52-07NA27344 between the U.S. Department of Energy and Lawrence Livermore National Security, LLC, for the operation of Lawrence Livermore National Laboratory.

BACKGROUND

New paradigms for early detection, prevention, and control at the human-environmental interface are needed to reduce global threats from current and emerging infectious diseases. For example, better storage and transport solutions are needed for pathogen-containing samples collected from global satellite laboratories, health clinics and military hospitals treating soldiers with persistent infections. While adequate collection and storage solutions are available for immediate transport to the laboratory, these methods are extremely time sensitive and often require refrigeration and/or cold storage.

Current methodologies for pathogen recovery and identification are dependent on obtaining sterile samples, which is often complicated in the field by contamination of the material with patient or environmental flora. In addition, existing methods are dependent on the use of pathogen-specific transport media, which delays identification of new emerging biothreats in the field, where no such defined growth media exists.

Thus, a need exists for safe and convenient method for the transport of pathogens at ambient temperatures. This disclosure satisfies this need and provides related advantages as well.

SUMMARY OF THE DISCLOSURE

Free-living amoebae are present worldwide, having been isolated from soil, fresh and salt water, and air. Amoebae are phagocytic and primarily feed on bacteria, fungi and algae. Some microorganisms have evolved to survive phagocytocis by amoebae and are known as Amoebae Resistant Microorganisms (ARM). In addition to *Legionella* and *Mycobacterium* spp., the list of ARM has recently been shown to include Mimiviruses and Enteroviruses. The amoeba, *Acanthamoeba castellanii*, is known to serve as a reservoir for a number of pathogenic microorganisms in nature, and to play a role in their environmental survival and dissemination. The ability of several human intracellular pathogens, including *L. pneumophila* and *M. avium*, to infect and survive within *A. castellanii* has been well characterized. Amoebae have also been shown to support the growth of many bacteria of interest to biodefense (e.g. *Francisella tularensis, Yersinia pestis, Coxiella bernetti*) as well as a number of emerging pathogens (e.g. *Klebsiella pneumoniae* and *Pseudomonas aeroginosa*) in the laboratory. Importantly, environmental bio-surveillance programs increasingly identify amoebae containing Viable Nonculturable Organisms (VNCO), this suggests that many ARM remain to be identified and that amoebae growth may induce the intracellular bacteria to enter a metabolically dormant state.

Amoebae are known to exhibit a biphasic life style, existing as trophozoites in presence of abundant nutrients and as cysts in response to desiccation and nutrient shortage. Multiple pathogens have been shown to persist in cysts for years and then emerge in response to favorable environmental conditions when the amoebae excyst. Amoebae cysts are composed of tough cellulose-like structures that are extremely resistant to biocide and mechanical lysis, which naturally protects any enclosed pathogens. In contrast to traditional transport media, where pathogens often lose virulence factors present on extrachromosomal elements such as plasmids or transposons, a number of studies have shown that growth in amoebae supports the virulence of ARM and their ability to invade and survive in host cells. This is believed to be due to similar selective pressures present in amoebae and mammalian cells. It is currently accepted that growth in amoebae provides an opportunity for intracellular pathogens to adapt to the intracellular niche enabling them to subsequently resist killing by mammalian host cells. Development of amoeba cysts as a transport system has the advantages of using an environmentally tolerant system that supports pathogen growth and virulence and is resistant to contamination with common skin flora.

Applicant provides a method for transporting a pathogen under ambient conditions, comprising, or alternatively consisting essentially of, or yet further consisting of, culturing the pathogen with an amoeba under conditions that favor the incorporation of the pathogen into a trophozoite of the amoeba and causing the trophozoite to encyst, and then culturing under conditions that favor conversion of the amoeba cyst to a trophozoite, which can release the engulfed pathogen. In one aspect, the conditions that favor incorporation of the pathogen into the cyst of the amoeba comprises contacting the pathogen with the amoeba in an iron rich environment. Virus and/or bacteria are pathogens that can be transported by the disclosed method. Amoeba that are useful in the disclosed methods include, without limitation *Acanthamoeba castellanii, Hartmannella vermiformis* and *Naegleria gruberi*.

Figure 3:
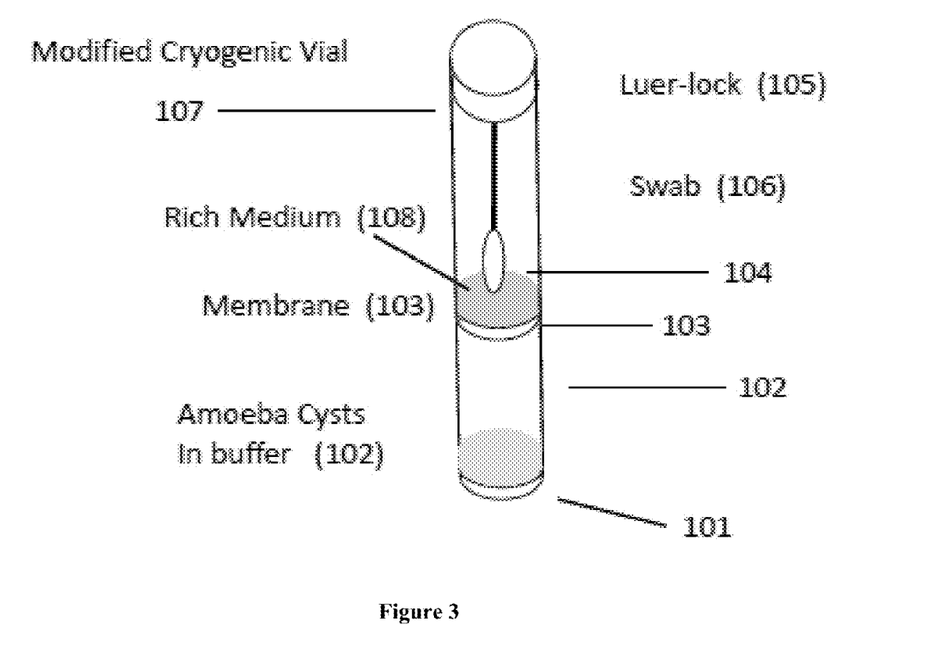
FIG. 3 depicts a device of this disclosure that can be utilized for the safe culturing and transport of the amoeba cysts.

Also provided by this disclosure is a substantially homogenous population or culture of amoeba trophozoites and/or cysts prepared by the above method which comprises, or alternatively consists essentially of, or yet further consists of, an exogenous pathogen encysted in a trophozoite and/or an amoeba cyst. The composition comprising the substantially homogenous population or culture can further comprise, or alternatively consist essentially of, or yet further consist of a carrier, such as buffer, media or a device, as shown in FIG. 3. This disclosure further provides a device as shown in FIG. 3 for culture and transport of pathogens.

The disclosed methods have utility in: transporting pathogens from military field hospitals and clinics to the laboratory; transporting pathogens from global satellite laboratories to clinical laboratories; long term storage of pathogens; enriching contaminated patient samples for pathogens of interest; bio-surveillance and detection efforts.

Further provided is a culture transport device comprising a housing having a first compartment and a second compartment, the first and second compartments being separated by a permeable membrane, wherein the second compartment comprises a removable cap comprising a sampling elongated member and a locking device, wherein when the locking device is activated, the permeable membrane is ruptured by the elongated member. In one aspect, the housing of the device is comprised of an impermeable temperature and pressure tolerant material such as polypropylene.

DETAILED DESCRIPTION

Definitions

The practice of the present invention will employ, unless otherwise indicated, conventional techniques of tissue culture, immunology, molecular biology, microbiology, cell biology and recombinant DNA, which are within the skill of the art. See, e.g., Sambrook, Fritsch and Maniatis (1989) Molecular Cloning: A Laboratory Manual, $2^{nd}$ edition; F. M. Ausubel, et al. eds. (1987) Current Protocols In Molecular Biology; the series Methods in Enzymology (Academic Press, Inc.): PCR 2: A Practical Approach (1995) (M. J. MacPherson, B. D. Hames and G. R. Taylor eds.); Harlow and Lane, eds. (1988) Antibodies, A Laboratory Manual; Harlow and Lane, eds. (1999) Using Antibodies, a Laboratory Manual; and R. I. Freshney, ed. (1987) Animal Cell Culture.

All numerical designations, e.g., pH, temperature, time, concentration, and molecular weight, including ranges, are approximations which are varied (+) or (−) by increments of 1.0 or 0.1, as appropriate. It is to be understood, although not always explicitly stated that all numerical designations are preceded by the term "about". It also is to be understood, although not always explicitly stated, that the reagents described herein are merely exemplary and that equivalents of such are known in the art.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above.

As used in the specification and claims, the singular form "a," "an" and "the" include plural references unless the context clearly dictates otherwise.

As used herein, the term "comprising" is intended to mean that the compositions and methods include the recited elements, but do not exclude others. "Consisting essentially of" when used to define compositions and methods, shall mean excluding other elements of any essential significance to the combination when used for the intended purpose. Thus, a composition consisting essentially of the elements as defined herein would not exclude trace contaminants or inert carriers. "Consisting of" shall mean excluding more than trace elements of other ingredients and substantial method steps. Embodiments defined by each of these transition terms are within the scope of this invention.

The term "isolated" means separated from constituents, cellular and otherwise, in which the cell, tissue, polynucleotide, peptide, polypeptide, protein, antibody or fragment(s) thereof, which are normally associated in nature. For example, an isolated polynucleotide is separated from the 3' and 5' contiguous nucleotides with which it is normally associated in its native or natural environment, e.g., on the chromosome. As is apparent to those of skill in the art, a non-naturally occurring polynucleotide, peptide, polypeptide, protein, antibody or fragment(s) thereof, does not require "isolation" to distinguish it from its naturally occurring counterpart. An isolated cell is a cell that is separated form tissue or cells of dissimilar phenotype or genotype.

The term "propagate" means to grow or alter the phenotype of a cell or population of cells. The term "growing" refers to the proliferation of cells in the presence of supporting media, nutrients, growth factors, support cells, or any chemical or biological compound necessary for obtaining the desired number of cells or cell type. In one embodiment, the growing of cells results in the regeneration of tissue.

The terms "culturing" or "incubating" refer to the in vitro propagation of cells or organisms on or in media of various kinds. It is understood that the descendants of a cell grown in culture may not be completely identical (i.e., morphologically, genetically, or phenotypically) to the parent cell. By "expanded" is meant any proliferation or division of cells.

A "composition" is also intended to encompass a combination of a compound or composition and another carrier, e.g., a solid support such as a culture plate or biocompatible scaffold, inert (for example, a culture plate) or active, such as an adjuvant, diluent, binder, stabilizer, buffers, salts, lipophilic solvents, preservative, adjuvant or the like. Carriers also include pharmaceutical excipients and additives proteins, peptides, amino acids, lipids, and carbohydrates (e.g., sugars, including monosaccharides, di-, tri-, tetra-, and oligosaccharides; derivatized sugars such as alditols, aldonic acids, esterified sugars and the like; and polysaccharides or sugar polymers), which can be present singly or in combination, comprising alone or in combination 1-99.99% by weight or volume. Exemplary protein excipients include serum albumin such as human serum albumin (HSA), recombinant human albumin (rHA), gelatin, casein, and the like. Representative amino acid/antibody components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like. Carbohydrate excipients are also intended within the scope of this invention, examples of which include but are not limited to monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol) and myoinositol.

"Substantially homogeneous" describes a population of amoeba in which more than about 50%, or alternatively more than about 60%, or alternatively more than 70%, or alternatively more than 75%, or alternatively more than 80%, or alternatively more than 85%, or alternatively more than 90%, or alternatively, more than 95%, or alternatively more than 97% of the amoeba are of the same or similar phenotype.

The term "effective amount" refers to a concentration or amount of a reagent or composition, such as a composition as described herein, cell population or other agent, that is effective for producing an intended result, including cell growth and/or differentiation in vitro or in vivo, or for the treatment of a disease or condition as described herein. It will be appreciated that the number of cells to be administered will vary depending on the specifics of the disorder to be treated, including but not limited to size or total volume/surface area to be treated, as well as proximity of the site of administration to the location of the region to be treated, among other factors familiar to the medicinal biologist.

The terms effective period (or time) and effective conditions refer to a period of time or other controllable conditions (e.g., temperature, humidity for in vitro methods), necessary or preferred for an agent or composition to achieve its intended result, e.g., the differentiation of cells to a predetermined cell type.

The term patient or subject refers to animals, including mammals, preferably humans, who are treated with the pharmaceutical compositions or in accordance with the methods described herein. Other animals include, simians, bovines, ovines, equines, canines, felines, and murines.

The term pharmaceutically acceptable carrier (or medium), which may be used interchangeably with the term biologically compatible carrier or medium, refers to reagents, cells, compounds, materials, compositions, and/or dosage forms that are not only compatible with the cells and other agents to be administered therapeutically, but also are, within the scope of sound medical judgment, suitable for use in contact with the tissues of human beings and animals without excessive toxicity, irritation, allergic response, or other complication commensurate with a reasonable benefit/risk ratio. Pharmaceutically acceptable carriers suitable for use in the present invention include liquids, semi-solid (e.g., gels) and solid materials (e.g., cell scaffolds and matrices, tubes sheets and other such materials as known in the art and described in greater detail herein). These semi-solid and solid materials may be designed to resist degradation within the body (non-biodegradable) or they may be designed to degrade within the body (biodegradable, bioerodable). A biodegradable material may further be bioresorbable or bioabsorbable, i.e., it may be dissolved and absorbed into bodily fluids (water-soluble implants are one example), or degraded and ultimately eliminated from the body, either by conversion into other materials or breakdown and elimination through natural pathways.

Methods

For the purpose of illustration only, *A. castellanii*, the select agent pathogen *Burkholderia pseudomallei*, and the emerging pathogen *Acinetobacter baumannii*, *A. castellanii* cysts can act as a natural transport system for pathogens from field locations to the laboratory at room temperature, e.g., from about 23° C. to about 45° C., or alternatively from about 23° C. to about 42° C., or about 37° C. These pathogens survive long-term in amoebae cysts and can be recovered post excystment for testing or other manipulation as desired. As shown in more detail below, Applicant has used the disclosed method to recover bacteria and confirmed phenotype to ensure no loss of viability or virulence. Non-limiting examples of bacteria for transport using the above method include, without limitation *A. baumannii* (Bouvet and Grimont ATCC 9955) and *B. pseudomallei*, (ATCC 23343).

Thus, in one aspect, Applicant provides a method for transporting a pathogen under ambient conditions e.g., from about 23° C. to about 45° C., or alternatively from about 23° C. to about 42° C., or about 37° C., comprising, or alternatively consisting essentially of, or yet further consisting of, culturing the pathogen with an amoeba under conditions that favor the incorporation of the pathogen into a trophozoite of the amoeba, causing the trophozoite to encyst, and then culturing under conditions that favor the conversion of the amoeba cyst to a trophozoite. As is apparent to those of skill in the art, a trophozite is the active feeding and motile stage of the ameboid while the cyst stage is the dormant, non-feeding or mobile stage in the life cycle.

Applicant has discovered that the conditions that favor incorporation of the pathogen into the trophozoite comprise or are enhanced by, or alternatively consist essentially of, or yet further consist of, contacting the pathogen with the amoeba in an iron rich environment. As used herein, the term "iron rich" intends an environment having, as compared to conventional media for the growth and/or maintenance of amoeba, at least 2×, or alternatively at 3×, or alternatively at least 4×, or alternatively at least 5×, or alternatively at least 6×, or alternatively at least 7×, or alternatively at least 8×, or alternatively at least 9×, or alternatively at least 10×, concentration of iron in the media, or alternatively from about 2× to 10×, or alternatively at least about 3× to 10×, or alternatively at least about 4× to 10×, or alternatively at least about 5× to 10×, or alternatively at least about 6 to 10× of an iron source in the media. Alternatively, the iron is present in an amount of at least about 0.005 M, or at least about 0.01M, or alternatively at least about 0.02M, or alternatively at least about 0.03M, or alternatively at least about 0.04M, or alternatively at least about 0.05M, or alternatively at least about 0.06M, or alternatively at least about 0.07M, or alternatively from about 0.01M to 0.07M, or alternatively from about 0.02M to about 0.06M, or alternatively from about 003M to about 0.06M, or alternatively about 0.05 M iron, e.g., 0.05M ferrous ammonium sulfate ($FeAmSO_4$).

Applicant has discovered that when the amoeba and the pathogen are cultured in conditions of iron rich environment, the amoeba quickly engulfs the pathogen. The culturing is accomplished under ambient conditions, depending on the environment of the pathogen. For example, the amoeba can be transported from a tropical location as a cyst and then converted to the active growing form (trophozoite) by adding nutrient rich media. Thus, the pathogen can be added to the amoeba under conditions that favor the growth and replication of the amoeba and the culture media is changed to nutrient rich and an iron source is added to the culture to provide the iron rich environment. When the nutrients in the culture media have been depleted, the amoeba will convert into a cyst, which is environmentally tolerant and can be easily transported. In a further aspect, antimicrobial or antibiotics can be added to remove all active pathogen in the culture just prior to or after cyst formation. As noted before, the trophozoite containing the pathogen will then encyst and can then be transported under ambient conditions. The cyst is converted back to the actively growing trophozoite form and the pathogen is released from the trophozoite by culturing the cysts under in iron and nutrient rich media. In one aspect, a solution to lyse the trophozoite, such as a 0.5% saponin solution can be used to release the pathogen from the trophozoite.

For the purpose of illustration only, Applicant has found that by culturing at least $0.5 \times 10^6$ or alternatively at least $1.0 \times 10^6$ pathogens per ml iron-rich media, the amoeba and pathogen will replicate and the amoeba will engulf the pathogen and convert to a cyst in several hours.

After the cyst is converted into an amoeba trophozoite, the pathogen are released into the culture media where they can be isolated and characterized using conventional microbial techniques.

The above methods are useful to transport virus or bacteria, e.g., *Legionella*, *Mycobacterium*, *Francisella*, *Yersinia*, *Coxiella*, *Klebsiella*, *Pseudomonas*, *Burkeholderia* and *Acinetobacer*. In one aspect, the amoeba is selected from the group consisting of *Acanthamoeba castellanii*, *Hartmannella vermiformis* and *Naegleria gruberi*. For added convenience, the entire process and transport can be accomplished in conventional modified cryopreservation vials (see FIG. 3).

This disclosure also provides a device or container for the safe transport and storage of pathogens or microbes using the methods as disclosed herein. As shown in FIG. 3, the device is a multi-compartment container containing at least 2 compartments having at least one removable cap or tip. The shape of the device is not critical to the design. For example, the container can be cylindrical. The outer walls of the container (housing) are made of an impermeable material that is resistant to temperature and pressure fluctuations. Examples of materials include without limitation polypropylene or other plastic. The at least two-compartment container is separated by a liquid impermeable membrane or barrier that is permeable to pressure. One cap that is removable has contained in it an elongated swabbing device, such as a cotton swab, for sampling the pathogen or microbe. It is fitted with locking device such as a a luer lock that when closed in the locked position, will push the swab containing the pathogen into the other compartment through the permeable membrane, e.g., a thin rubber, plastic or the like. At least one other compartment is configured to contain the amoeba cysts in a buffer solution and while the other is configured to contain the iron and nutrient rich medium. When needed, the cap is removed and one compartment is opened. The swab is used to collect the sample. The swab is returned to the inside of the container and it is locked using the locking device such as the luer lock, or any other two step lock, thereby forcing the swab through the membrane and allowing the nutrient rich medium to fall into the other compartment. Mixing the container will bring the amoeba cysts in the bottom compartment to contact the iron-rich medium and the sample resulting in amoeba excystment and microbial phagocytosis by amoeba trophozoites.

Using FIG. 3 as example, shown therein is a two compartment cylindrical container having a compartment (101) that contains the amoeba in buffer (102). An additional compartment (104) has at one end a removable cap (107) with a sampling device or swab (106) and iron rich media (108). The cap (107) contains a locking device (105). Separating the compartment is permeable membrane (103) that is punctured when the locking device (105) of the cap is activated allowing the iron rich media to flow from one compartment (104) into the other (101) and the pathogen and the amoeba to come in contact with each other.

Materials and Methods

Media

Rich Media: Modified Peptone-Yeast-Glucose (PYG)

| | |
|---|---|
| Protease peptone | 20 g |
| Yeast Extract | 1 g |
| Add 900 ml of dd H$_2$O. Autoclave and cool down to at least 55° C. | |
| Add the following: | |
| Sodium citrate | 1 g |
| 0.4M Magnesium Sulfate (MgSO$_4$) | 10 ml |
| 0.05M Calcium chloride (CaCl$_2$) | 8 ml |
| 0.05M Ferrous Ammonium Sulfate (FeAmSO$_4$) | 10 ml |
| (Filter sterilize, do not autoclave) | |
| 0.25M Dibasic Sodium phosphate ((Na)$_2$HPO$_4$) | 10 ml |
| 0.25M Monobasic Potassium phosphate (KH$_2$PO$_4$) | 10 ml |
| Adjust pH to 6.5 exactly. Add 50 ml of 2M glucose. Filter sterilize through a 0.22 µm filter. | |

High Salt Buffer

Mix the Following:

| | |
|---|---|
| Sodium citrate | 1 g |
| 0.4M Magnesium Sulfate (MgSO$_4$) | 10 ml |
| 0.05M Calcium chloride (CaCl$_2$) | 8 ml |
| 0.05M Ferrous Ammonium Sulfate (FeAmSO$_4$) | 10 ml |
| (Filter sterilize, do not autoclave) | |
| 0.25M Dibasic Sodium phosphate ((Na)$_2$HPO$_4$) | 10 ml |
| 0.25M Monobasic Potassium phosphate (KH$_2$PO$_4$) | 10 ml |

Add 950 ml of dd H$_2$O. Adjust pH to 6.5 exactly. Filter sterilize through a 0.22 µm filter.

The ability of *B. pseudomallei* (Bp) and *A. baumannii* (Ab) isolates to survive in *A. castellanii* (AC) trophozoites and cysts can be confirmed by conducting infection and intracellular survival assays. For example, amoeba trophozoites are grown in Peptone-Yeast-Glucose medium at room temp (RT) in the dark. Amoeba are then seeded at a concentration of approximately $10^5$ per ml per well in 24-well plates in PYG broth at room temperature.

Bacteria are grown overnight (o/n) in Nutrient broth (NB for both Ab and Bp) available from Difco-Invitrogen) broth at 37° C. with shaking.

The PYG medium can be removed by aspiration from the Ac plates and replaced by 1 ml of High Salt Buffer (HSB) per well and the plates incubated at 37° C. for 1 hr. 100 µl of bacterial cultures are added per amoeba well to achieve a multiplicity of infection (MOI) of 10 and then incubated for 30 min at 37° C. to allow bacterial internalization then washed 1× with HSB. Media is replaced by fresh HSB containing 100 µg/ml gentamicin and the plates incubated for 2 hours to kill extracellular bacteria. Chloroamphenicol can be used for gentamicin resistant strains.

The amoeba will is washed 1× with HSB then lysed with 0.5% Saponin release intracellular bacteria. Conventional microbiological techniques, such as plating on nutrient agar plates can be used to determine bacterial colony forming units (CFU).

To determine intracellular survival, 1 ml of fresh HSB can be added to parallel wells instead of immediate lysis at time point zero. Wells are then incubated for varying time points prior to lysis and platting.

% bacterial survival=CFU at 24 hr/CFU at time zero

Amoeba trophozoites typically encyst within 2 days after nutrient depletion. To confirm the ability of the bacteria to survive long term in amoeba cysts, plates can be incubated at temperatures ranging from 4° C. to 42° C. to demonstrate environmental tolerance. One set of wells can be lysed at weekly time points. At each time point, amoeba cysts will be centrifuged for 5 min at 1000 g. The medium will be decanted and replaced with PYG to allow excystment. Amoeba cysts are incubated at 37° C. until the first sign of turbidity or for 48 hours to allow the amoeba to excyst and the bacteria to be released into the medium. Intracellular bacteria can be recovered by platting dilutions on nutrient agar.

Genetic Stability and Storage

To confirm the suitability of *A. castellanii* cysts to function as a transport system for pathogens, four isolates of *Burkholderia pseudomallei* and one isolate of *Acinetobacter baumanii* were sequenced before and after they were grown in amoebae for one month, and the genomic sequences compared to identify any genetic differences. The Illumina Hi-Seq 2000 platform was used for sequencing and at least 100× genome coverage was targeted to ensure high confidence mutation analysis in the isolates. A preliminary analysis of the *A. baumanii* isolates and one pair of the *B. pseudomallei* isolates follows.

*A. baumanii*

The Burrows-Wheeler Aligner (BWA) program was used to align the sequence reads from both isolates against the Reference Sequence genome for *A. baumannii* strain ACICU. A custom code was developed to count the nucleotides of each type that aligned to each reference genome position, plus the numbers of deletions (gaps) at each position. This produced a table of allele frequencies for each isolate at each position. The code then looked for positions where the major allele differed between the isolates. Out of 3.9 MB in the reference genome, about 29,000 such positions were identified.

Positions that had 5 or fewer reads were filtered out from either isolate mapped to them, since allele frequency estimates based on small read counts are inherently unreliable. This excluded all but the 331 locations. For each location, a chi-squared statistic and associated P-value were computed, estimating the probability that the observed difference in observed allele frequencies between the un-passaged and amoeba-passaged isolates could have occurred by chance.

Of immediate note is that, for almost all positions selected for candidate mutations, the major allele frequency ranges from 45% to 65%; there is only one site (1891835) where 100% of the reads have one allele in the un-passaged isolate and a different allele for most of the reads in the passaged isolate. Sorting the table in descending order of major allele frequency for the un-passaged isolate, reveals that the 3 positions with the highest major allele frequency (MAF) all have relatively small numbers of reads mapped to them. Any evidence for actual mutations at these sites is pretty weak.

In addition, when re-sorting the table by genome position, Applicant noted that the locations of the candidate mutations were clustered into small genome regions. The distribution of these regions suggested that they map to insertion (IS) elements, or other repeated sequences. On examining the GenBank annotations for the *A. baumannii* ACICU genome, positions 262878-264180 was annotated as a hypothetical protein. However, when performing BLAST queries of this protein sequence against GenBank data, it was found that analogous proteins are annotated as antibiotic resistance islands, genomic resistance islands and transposons. These data suggest that *A. baumanii* reads mapping to this region are hitting a transposon with an imperfect copy elsewhere in the genome, i.e., BWA could be mapping them arbitrarily to either copy, giving the appearance of a mixed population.

Another region, 1109338-1165207, is somewhat larger (56 kB), and maps to multiple genes, so it's less obvious that there it is a repeat sequence. However, generation of a dotplot from performing BLAST queries of the ACICU genome against itself indicates a string of duplicated sequences; one set of copies in the region 1150000-1155000, the other from 2900000-2935000 (which includes the other large stretch of candidate mutations). These data suggest a similar pattern, where reads are mapped arbitrarily to the different copies and thus appear to indicate mutations, when actually they're just reflecting the variation between paralogs.

In summary, our initial analyses suggest that all the candidate mutations observed are resulting either from either noise variation when the number of mapped reads is small, or from variation between paralogs within the reference genome. So at least for this pair of isolates, there is no evidence for mutations resulting from growth in amoebae.

*B. pseudomallei*

Similar to the approach used for *A. baumannii* isolates, BWA was used to align the sequence reads from the two isolates of *B. pseudomallei* strain PHLS17—one passaged in amoeba and the other grown in standard lab broth—against the Reference Sequence genome for *B. pseudomallei* strain K96243. A custom program was created to tabulate, at each position in the two K96243 chromosomes, the allele frequencies for each nucleotide and the frequency of deletions (gaps). About 29,000 positions (out of 7.1 million) for which the major allele differed between the two sets of reads. However, these differences are unlikely to represent actual mutations. Since *B. pseudomallei* are characterized by extensive recombination and duplication of genome regions, many sequence reads (about 35,000 in this case) align to multiple locations in the genome. Subsequent mutations in the duplicated regions in distant ancestors of the current PHLS17 strain cause slight variations between the multiple genome sequences aligned to a sequence read. Similar to our observations on the analysis of the *A. baumannii* sequences, these variations between paralogous regions can masquerade as mutations between isolates. *B. pseudomallei* genomes have vastly more internal duplication than *A. baumannii* genomes, so the number of potential false mutations is much larger.

Long Term Stability

*F. tularensis*

In contrast to *B. pseudomallei* and *A. baumanii*, *F. tularensis* is a very fastidious organism that is often hard to grow in the laboratory. The Schu S4 strain, which is the typical type A strain used in research, was used as well as three clinical strains isolated from human Tularemia outbreaks in Utah and minimally manipulated in the laboratory. One of these strains (80700069) has been identified as type A2, while the rest are all type A1 strains. Previous work has shown that all these strains are capable of entry and replication within amoeba (El-Etr, et. al., (2009) AEM, 75:7488-7500). In addition, with the exception of strain 80700069, all the strains cause the rapid encystment of *A. castellanii*.

All clinical strains are shown to survive intracellularly in amoeba cysts up to six weeks post infection (Table 1) at temperatures ranging from 26 to 42° C. The Schu S4 strain was not recovered from amoeba cysts after three weeks post infection. This observation may be explained by the fact that the Schu S4 strain has been propagated under laboratory conditions for almost 70 years since its initial isolation from a clinical case and that some loss of virulence is to be expected.

TABLE 1

Recovery of *F. tularensis* type A strains from amoeba cysts at weekly intervals after initial infection. NG denotes no growth in experimental wells after addition of rich medium, plus signs indicate successful bacterial recovery and A1 or A2 indicates strain type.

| Strain | Week 1 | Week 2 | Week 3 | Week 4 | Week 5 | Week 6 |
|---|---|---|---|---|---|---|
| SchuS4 (A1) | + | + | + | NC, | NC, | NG |
| 70102163(A1) | + | + | + | + | + | + |
| 80700069 (A2) | + | + | + | + | + | + |
| 80502541 (A1) | + | + | + | + | + | + |

*B. mallei*

Though not as fastidious as *F. tularensis, B. mallei* strains are not as environmentally tolerant as *B. pseudomallei* and for a long time the organisms were thought to have a strict requirement for a mammalian host. Recent data from Australia however indicate the organism may survive long enough in the environment to infect incidental hosts.

Two strains of *B. mallei* from the ATCC were used to investigate the ability to survive and replicate in amoeba (ATCC (15310 and 10399) and two clinical strains isolated from India and Turkey. Of these strains, only the Turkish strain (NCTC 10260) is known to be isolated from an infected human, the Indian strain having been isolated from a mule. The rest of the strains have been isolated from horses, the natural hosts of *B. mallei.*

The data indicate that all the *B. mallei* strains we tested can survive and replicate well in amoeba which has never been reported before.

Long-term growth experiments examining the ability of *B. mallei* strains to survive in amoeba cysts indicate that all the strains tested are able to survive for 3 weeks post infection at temperatures ranging from 26 to 42° C. (Table 2). Although clinical strains were recovered up to six weeks post infection, recovery of the ATCC strains after three weeks was inconsistent, especially at 42° C. which may again be explained by loss of virulence since both strains were originally isolated more than 50 years ago.

TABLE 2

Recovery of *B. mallei* strains from amoeba cysts at weekly intervals after initial infection NG denotes no growth in experimental wells after addition of rich medium, plus signs indicate successful bacterial recovery.

| | Week 1 | Week 2 | Week 3 | Week 4 | Week 5 | Week 6 |
|---|---|---|---|---|---|---|
| ATCC 15310 | + | + | + | NG | NG | NG |
| ATCC 10399 | + | + | + | NG | NG | NG |
| NCTC 10260 | + | + | + | + | + | + |
| CDC 85 | + | + | + | + | + | + |

On a final note, even though both *F. tularensis* and *B. mallei* clinical strains can survive in amoeba cysts up to six weeks, recovery of the bacterial isolates after transport has yet to be done at 37° C. in the laboratory. Attempts to recover both pathogens at higher temperatures were not successful, possibly due to the sensitivity of both organisms to high temperatures when they are not protected inside amoebae cysts.

Sampling and Transport of Skin Flora

Experiments were performed with *A. baumanii* and *B. pseudomallei* in presence of human skin flora. Sterile cotton swabs were wetted with HSB and used to collect skin flora from the forearms of healthy adult volunteers. The collected bacteria were used to inoculate 1 ml of HSB and the samples were randomized then numerically labeled per IRB requirements. An aliquot of the buffer was then plated directly on nutrient agar (to determine number of bacteria added) and the rest inoculated with dilutions of either *A. baumanii* or *B. pseudomallei* cultures and added to$10^6$ amoeba trophozoites previously seeded overnight. The amoebae were then incubated for 30 days at temperatures ranging from 26 to 42° C. The dilutions of *A. baumanii* or *B. pseudomallei* cultures were also plated to determine the bacterial numbers added. After one month, rich media was added to all wells. Upon observing signs of turbidity, dilutions of the supernatants were plated to assess colony-forming units (cfu) as well as streaked for isolation to enable gram staining and bacterial identification.

Results indicate that in each experiment, Applicant was able to detect as little as 430 cfu *A. baumanii* (Table 3) or 177 cfu of *B. pseudomallei* (Table 4). This makes the multiplicity of infection <0.001 (MOI number of bacteria/number of amoeba). These results were consistent at temperatures ranging from 26 to 42° C. In addition, in almost all cases the amoebae were able to consume all the skin bacteria while preserving the pathogen. With the exception of one case (Table 4, Subject 9) negligent amounts of flora were recovered. The amoeba was therefore able to purify the sample from skin flora and enrich for the pathogen of interest. Interestingly, analysis of the colonies recovered from subject 9, showed that more than 95% of the skin colonies recovered were *Staphylococcus aureus* indicating the subject was a carrier thereby giving us positive preliminary data about the ability of gram-positive pathogens to survive in amoebae cysts.

TABLE 3

*A. baumanii* and bacterial skin flora recovered after incubation in amoebae cysts for one month. "Added" represents the cfu of *A. baumanii* or skin flora inoculated into amoebae cysts. "Recovered" represents the cfu recovered after a 30-day incubation. TNTC: cfu too numerous to count >1000 cfu.

| *A. baumanii* added/ recovered | Subject 1 added/ recovered | Subject 2 added/ recovered | Subject 3 added/ recovered | Subject 4 added/ recovered | Subject 5 added/ recovered | Subject 6 added/ recovered |
|---|---|---|---|---|---|---|
| $4.3e^7$/TNTC | 268/0 | 48/0 | 27/2 | 89/0 | 64/1 | 37/0 |
| $4.3e^6$/TNTC | 268/1 | 48/0 | 27/0 | 89/1 | 64/0 | 37/0 |
| $4.36^5$/TNTC | 268/3 | 48/1 | 27/0 | 89/0 | 64/2 | 37/1 |
| $4.3e^4$/TNTC | 268/0 | 48/2 | 27/0 | 89/0 | 64/0 | 37/0 |
| $4.36^3$/TNTC | 268/0 | 48/0 | 27/0 | 89/2 | 64/0 | 37/0 |
| $4.3e^2$/TNTC | 268/0 | 48/0 | 27/0 | 89/0 | 64/0 | 37/0 |

TABLE 4

B. pseudomallei and bacterial skin flora recovered after incubation in amoebae cysts for one month. "Added" represents the cfu of B. pseudomallei or skin flora inoculated into amoebae cysts. "Recovered" represents the cfu recovered after a 30-day incubation. TNTC: cfu too numerous to count >1000 cfu.

| B. pseudomallei added/recovered | Subject 1 added/recovered | Subject 2 added/recovered | Subject 3 added/recovered | Subject 4 added/recovered | Subject 5 added/recovered | Subject 6 added/recovered |
|---|---|---|---|---|---|---|
| $4.3e^7$/TNTC | 268/0 | 48/0 | 27/2 | 89/0 | 64/1 | 37/0 |
| $4.3e^6$/TNTC | 268/1 | 48/0 | 27/0 | 89/1 | 64/0 | 37/0 |
| $4.3e^5$/TNTC | 268/3 | 48/1 | 27/0 | 89/0 | 64/2 | 37/1 |
| $4.3e^4$/TNTC | 268/0 | 48/2 | 27/0 | 89/0 | 64/0 | 37/0 |
| $4.3e^3$/TNTC | 268/0 | 48/0 | 27/0 | 89/2 | 64/0 | 37/0 |
| $4.3e^2$/TNTC | 268/0 | 48/0 | 27/0 | 89/0 | 64/0 | 37/0 |

| B. pseudomallei added/recovered | Subject 7 added/recovered | Subject 8 added/recovered | Subject 9 added/recovered | Subject 10 added/recovered | Subject 11 added/recovered | Subject 12 added/recovered |
|---|---|---|---|---|---|---|
| $1.77e^4$/TNTC | 115/0 | 87/1 | 287/13 | 109/2 | 16/0 | 71/0 |
| $1.77e^6$/TNTC | 115/0 | 87/0 | 287/37 | 109/1 | 16/0 | 71/0 |
| $1.77e^5$/TNTC | 115/2 | 87/0 | 287/28 | 109/0 | 16/0 | 71/0 |
| $1.77e^4$/TNTC | 115/1 | 87/1 | 287/32 | 109/2 | 16/1 | 71/1 |
| $1.77e^3$/TNTC | 115/0 | 87/0 | 287/43 | 109/0 | 16/0 | 71/0 |
| $1.77e^2$/TNTC | 115/0 | 87/0 | 287/38 | 109/0 | 16/0 | 71/0 |

Changes in Antimicrobial, Biocide Resistance and Macrophage Survival to Ensure Lack of Phenotypic and Virulence Changes During Amoebae Growth.

Figure 1:
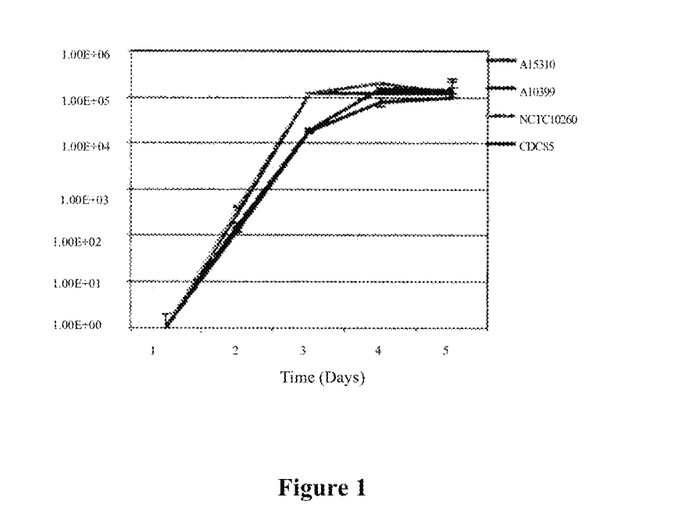
FIG. 1 illustrates growth in *B. mallei* strains in amoeba trophozoites. Time points were taken daily and reflect the means and standard deviations of triplicate assays. All experiments were conducted at least 3 times. % Survival=cfu at Tx/cfu at TOX100.
Figure 2:
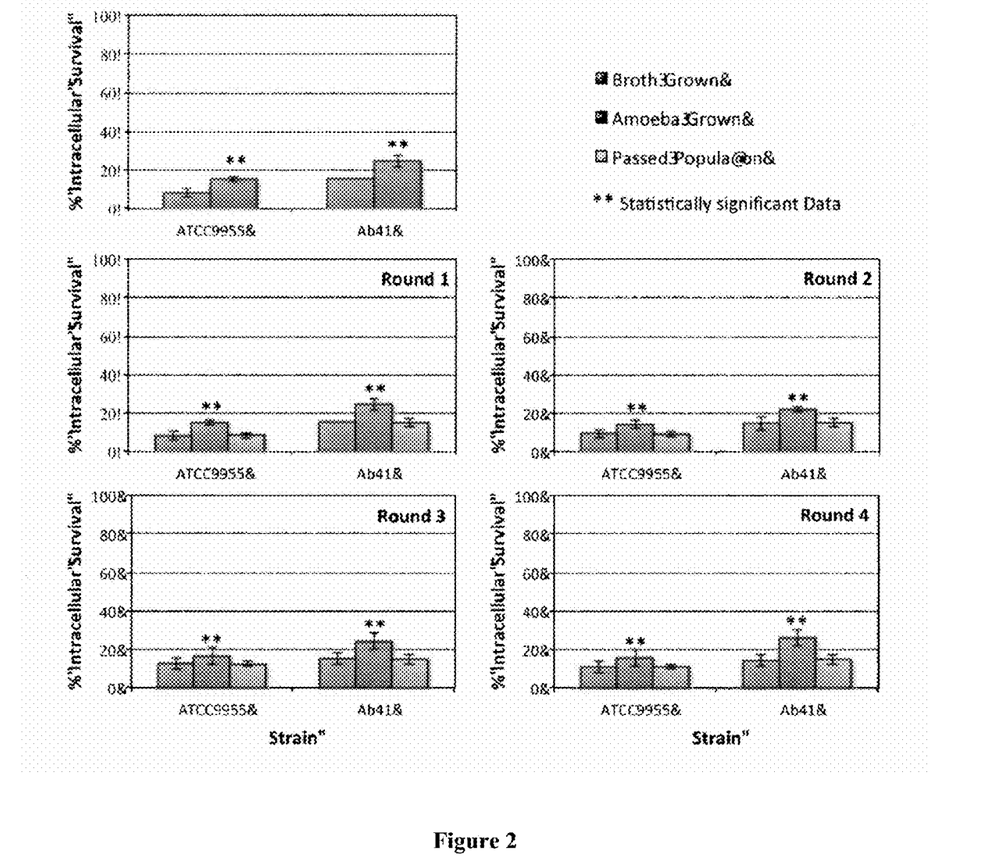
FIG. 2 illustrates survival of a cyclically passaged population of *B. pseudomallei* in human primary monocytes. The population was grown in amoeba cysts for 21 days, harvested then grown in lab media for 24 hours before being used to infect fresh amoeba again. At each passage an aliquot of the passaged population was used to infect human monocytes in parallel to lab-grown bacteria and freshly harvested amoeba-grown bacteria. Histograms and error bars represent the means and standard deviations of assays done in triplicate. Asterisks indicate the only statistically significant differences between samples.

Applicant has shown that survival in amoebae cysts does not increase the resistance Acinetobacter baumannii and Burkholderia pseudomallei to biocides and antimicrobials. To determine whether the enhancement in the ability of B. pseudomallei to survive in macrophages is a permanent change, amoeba-grown bacteria was inoculated into nutrient broth and grown under standard laboratory conditions for 24 hr. The bacteria were then used to re-infect fresh amoeba trophozoites. This cycle was repeated four times and at the end of each cycle the passaged B. pseudomallei population was tested for macrophage survival in parallel to regular lab-grown bacteria and bacteria freshly harvested from amoeba. The results show that after each passage in the lab media the survival of amoeba-grown bacteria returned to the levels of the broth grown strain within 24 hours (FIG. 2). These data suggest that the observed survival is due to gene regulation rather than to permanent mutations.

It should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be within the scope of this. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

REFERENCES

1. Rodriguez-Zaragoza S (1994) Ecology of free-living amoebae. Crit Rev Microbiol 20: 225-241.
2. Greub G, Raoult D (2004) Microorganisms resistant to free-living amoebae. Clin Microbiol Rev 17: 413-433.
3. Cirillo J D, Falkow S, Tompkins L S (1994) Growth of Legionella pneumophila in Acanthamoeba castellanii enhances invasion. Infect Immun 62: 3254-3261.
4. Goy G, Thomas V, Rimann K, Jaton K, Prod'hom G, et al. (2007) The Neff strain of Acanthamoeba castellanii, a tool for testing the virulence of Mycobacterium kansasii. Res Microbiol 158: 393-397.
5. El-Etr S H, Margolis J J, Monack D, Robison R A, Cohen M, et al. (2009) Francisella tularensis type A strains cause the rapid encystment of Acanthamoeba castellanii and survive in amoebal cysts for three weeks postinfection. Appl Environ Microbiol 75: 7488-7500.

What is claimed is:

1. A transport population or culture of amoeba capable of encysting a pathogen, in a two compartment container, the container comprising:
   a) a first compartment that has at one end a removable cap with a locking device to which is attached an elongated sampling device or swab member and wherein the first compartment comprises iron rich media,
   b) a second compartment comprising the amoeba in a buffer,
   c) a pathogen sample, and
   d) a permeable membrane that separates the container into the two compartments that is ruptured by the elongated member when the locking device is activated allowing the mixing of the iron rich media, the pathogen sample and the amoeba.

2. The population or culture of claim 1, wherein the pathogen is selected from the group consisting of a virus or a bacterium.

3. The population or culture of claim 1, wherein the pathogen is selected from the group consisting of *Legionella, Mycobacterium, Francisella, Yersinia, Coxiella, Klebsiella, Pseudomonas, Burkeholderia* and *Acinetobacer.*

4. The population or culture of claim 1, wherein the amoeba is selected from the group consisting of *Acanthamoeba castellanii, Hartmannella vermiformis* and *Naegleria gruberi.*

5. A culture transport device comprising a housing having a first compartment and a second compartment, the first and second compartments being separated by a permeable membrane, wherein the first compartment comprises an iron rich media and the second compartment comprising a population of amoeba in a buffer, a removable cap comprising a sampling elongated member and a locking device, wherein when the locking device is activated, the permeable membrane is ruptured by the elongated member.

6. The device of claim 5, wherein the housing of the device is comprised of an impermeable material.

7. The device of claim 6, wherein the impermeable material is polyethylene.

8. The culture transport device of claim 5, wherein the housing of the device is comprised of an impermeable material.

9. The population or culture of claim 8, wherein the impermeable material is polyethylene.

10. The culture transport device of claim 5, wherein iron-rich media comprises media comprising at least 2× concentration of iron.

11. The culture transport device of claim 5, wherein the amoeba is selected from the group consisting of *Acanthamoeba castellanii, Hartmannella vermiformis* and *Naegleria gruberi.*

12. A method for transporting a pathogen, comprising
Contacting a pathogen with the elongate swabbing member of the device of claim 5 and inserting the swab and the pathogen into the second compartment of the device by rupturing the permeable membrane and closing the cap and engaging the locking member.

* * * * *